US005807561A

United States Patent [19]

Guerrero

[11] Patent Number: 5,807,561

[45] Date of Patent: Sep. 15, 1998

[54] EMULSIFYING SYSTEM FOR A WHITENING COSMETIC COMPOSITION

[75] Inventor: Angel Augusto Guerrero, Huntington, Conn.

[73] Assignee: Elizabeth Arden Co., Division of Conopco, Inc., New York, N.Y.

[21] Appl. No.: 833,179

[22] Filed: Apr. 4, 1997

Related U.S. Application Data

[63] Continuation-in-part of Ser. No. 652,058, May 23, 1996, abandoned.

[51] Int. Cl.[6] .................................................... A61K 7/48

[52] U.S. Cl. ............................ 424/401; 424/59; 424/62; 514/844; 514/944

[58] Field of Search ............................ 424/401, 59, 62; 514/844, 944

[56] References Cited

U.S. PATENT DOCUMENTS 4,696,813 9/1987 Higa .......................................... 424/59

5,425,939 6/1995 Guerro et al. ........................ 424/78.02

FOREIGN PATENT DOCUMENTS 4-41409 2/1992 Japan .

*Primary Examiner*—Jyothsna Venkat

*Attorney, Agent, or Firm*—Milton L. Honig

[57] ABSTRACT

A cosmetic composition useful for enhancing a whitening effect on skin is described. The composition includes from 0.05 to 3 wt. % of a thickening polymer; from 1 to about 10 wt. % of the emulsifying system selected from the group consisting of a polyethylene glycol ether of cetearyl alcohol having a formula R $(OCH_2)_nOH$ wherein R is a straight or branched alkyl group having a chain length from 10 to 20 and n is 10–30; an ethoxylated alcohol selected from the group consisting of a $C_{12}$ to $C_{20}$ fatty acid polyethylene glycol ester having from 5 to 10 EOs; and a mixture of a cetearyl alcohol and a cetearyl glycoside. The preferred whitening agent is placenta extract.

6 Claims, No Drawings

EMULSIFYING SYSTEM FOR A WHITENING COSMETIC COMPOSITION

This is a continuation-in-part application of U.S. Ser. No. 08/652,058 filed May 23, 1996, now abandoned.

FIELD OF THE INVENTION

The invention relates to an emulsifying system for cosmetic compositions, particularly those compositions for enhancing a whitening effect of the skin.

BACKGROUND OF THE INVENTION

A variety of whitening cosmetics have been described for the removal of spots such as freckles which appear on the skin and to exhibit a whitening effect on the skin as a whole. Recent formulations have included a placenta extract ingredient as the active ingredient to enhance whitening used either alone or in combination with other agents, such as kojic acid (U.S. Pat. No. 4,696,813-Sansho Seiyaku kk) with iso-flavon glycoside components (JP 7 157 494) and ascorbic acid (JP 4 041 409-1992) to name just a few.

However, when these whitening agents are formulated with other cosmetic ingredients, such as water-soluble vitamins and concentrated botanical extracts a high level of electrolytes is brought into the composition. Emulsifiers are added to the formulas to both stabilize the products and serve as emollients to provide a smooth, aesthetically pleasing, and mild tactile feeling when the emulsified composition is applied to the skin. Emulsifiers in low pH systems are particularly sensitive to destabilization in a high electrolyte environment as products tend to separate into water soluble and insoluble phases due to the detrimental effect of the ions on the interfacial film.

However, thus among the myriad of emulsifying agents known in the art, an emulsifying system has continued to elude cosmetic formulators which is both mild and stable in the presence of electrolytes and in low pH systems.

It is thus an object of the present invention to provide an emulsifying system for a cosmetic composition, particularly compositions useful for whitening skin, which is aesthetically pleasing and mild to consumers.

It is another object of the present invention to provide an emulsifying system for a cosmetic composition that will remain stable during storage even in the presence of cosmetic ingredients with significant electrolytic behavior.

It is another object of the present invention to provide an emulsifying system for cosmetic compositions that are effective at low pH.

These other objects will become more readily apparent in the description and examples which follow.

SUMMARY OF THE INVENTION

A cosmetic composition useful for enhancing a whitening effect on skin is provided which includes:

a) from 0.05 to 3 wt. % of a thickening polymer selected from the group consisting of sclerotium gum and xanthan gum and mixtures thereof;

b) from 1 to about 10 wt. % of an emulsifying system selected from the group consisting of:

(i) a polyethylene glycol ether of cetearyl alcohol having a formula

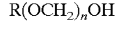

$R(OCH_2)_nOH$ wherein R is a straight or branched alkyl group having a chain length of from 10 to 20 and n is 20–30, (ii) an ethoxylated alcohol selected from the group consisting of a $C_{12}$ to $C_{20}$ fatty acid polyethylene glycol ester having from 5 to 10 EOs, and (iii) a mixture of a cetearyl alcohol and a cetearyl glycoside, the ratio of the compounds of (i) to (ii) to (iii) being from about 2:6:5 to about 3:7:6; and c) from 1 to 99.9% of a cosmetically acceptable carrier.

The components of the emulsifying system synergistically interact to form a stable gel network and a strong, sterically protected interfacial film, that stabilizes the system in the presence of a high content of electrolytes.

The emulsifying system of the compositions according to the invention is particularly effective at a pH between about 8.00 and 2.0, more preferably 5.5 to 3.5. The compositions also contain whitening agents, such as placenta extract, and oil soluble vitamins and botanical extracts.

DETAILED DESCRIPTION OF PREFERRED EMBODIMENTS

The cosmetic compositions of the present invention are applicable mainly as cosmetics for the skin such as lotion, creme, emulsion, pack, etc. The emulsifying system of the invention is prepared and combined a whitening agent, and the mixture is incorporated into a base conventionally used for cosmetics.

A highly effective emulsifying system useful for the described cosmetic composition must comprise three components, namely, a mixture of a specified fatty alcohols and an alkyl glycoside, an ethoxylated fatty alcohol and an ester of C12–20 fatty acids.

The first critical element is a mixture of fatty alcohols and an alkyl glycoside. The fatty alcohols have chain lengths ranging from 8 to 24, predominantly (i.e. greater than 50%), $C_{16}$ to $C_{18}$. Preferably the fatty alcohols are cetyl and stearyl alcohols. The fatty alcohols are mixed with the alkyl glycoside in a ratio of 65–90 to 35–10. Preferably the alkyl groups of the glycoside are alkylated with cetearyl alcohol. Commercially the alcohol and glucoside mixture is available under the trademark Montanov 68 from Seppic. Amounts of this material may range from about 0.15 to about 4.5 wt. %, preferably from about 0.35 to about 3.5 wt. %, optimally from about 0.5 to about 2.5 by wt.

A second essential element of the emulsifying system is an ethoxylated alcohol having from about 10 to about 25, preferably 18 to 22 EOs. Preferably the alcohol is cetearyl alcohol modified to form the polyethylene glycol ether of the alcohol. A preferred ethoxylated alcohol is commercially available under the trademark Eumulgin® from Henkel Corp. The ethoxylated alcohol may range from about 1.5% to about 8%, preferably 2 to about 5%, optimally from about 2 to about 4% by weight.

The third critical element of the emulsifying system is a polyethylene glycol ester of a $C_{12}$ to $C_{20}$ fatty acid having from 1 to 20, preferably 1 to 10 EOs. The ester may be obtained commercially under the trademark Xalifin 15 supplied by Laboratory Vevy Spa. The material is used in a range from about 0.10 to about 5.0, preferably from about 0.50 to about 3.00, optimally from about 1 to about 2.0% by weight.

The ratio of the three critical elements of the emulsifying system should be about 2:6:5 to about 3:7:6, preferably 1:2:1 to about 1:2:3, optimally 1:1:1 to about 1:3:3.

The placenta extract employed in the present invention has whitening agents which may be obtained by any means conventionally used in the art such as the method described in U.S. Pat. No. 4,696,813. Placental extract is also commercially available under the trademark BIO-BPL supplied by Ikeda Corporation. Placental extracts should be present in the composition in an amount of from about 0.5 to about 10 wt. %, preferably 1 to about 5 wt. %, optimally from about 2 to about 5 wt. %.

Various thickening agents are also present in the invention. Preferably xanthan gum and a sclerotium gum (CTFA name) which is a polymerized glucose is incorporated. This capsular β-D-glucan can be produced from a variety of fungi grown in media containing either glucose or sucrose as carbon sources and complex nitrogen sources supplemented with mineral oil. Glucan with an estimated degree of polymerization around 100 is obtained with *Sclerotium Glucincum* or with a degree of polymerization around 800 from a strain of *Sclerotium Rolfsii.* Commercially, a sclerotium gum derived from *Sclerotium Rolfsii* is available under the trademark Amigel® from Alban Muller/Tri K of France. Amounts of this material may range from about 0.05 to about 3%, preferably from about 0.10 to about 1.0%, optimally from about 0.20 to about 0.5% by weight.

Compositions of the present invention may include an aqueous phase or be totally aqueous. Advantageously, the pH of such aqueous systems may range from about 8.0 down to 2.0, preferably ranging from about 7.0 to about 4.0, optimally from about 5.5 and 3.5. A conventional buffering agent such as a mixture of citric acid and trisodium citrate, may be added to stabilize the desired pH. Other buffering agents include sodium phosphate, monosodium dihydrogen phosphate, disodium monohydrogen phosphate.

Water-soluble vitamins may also be incorporated in the invention which function as electrolytes. The term water-soluble defines substances with the solubility of at least 0.1%, preferably at least 1%, optimally at least 5% by weight in water. Illustrative water soluble vitamins are niacin, vitamin $B_2$, vitamin $B_6$, vitamin C, and biotin. The total amount of vitamins in the compositions may range from about 0.001 to about 1%, preferably from about 0.01 to about 0.6%, optimally from about 0.1 to about 0.5% by weight.

Two classes of keratolytic agents may also be effectively used in compositions of the present invention. The first category is represented by $C_7$—$C_{30}$ β-hydroxy carboxylic acids and their salts. Illustrative of this category is salicylic acid as well as the alkalimetal and ammonium salts thereof. Suitable amounts of salicylic acid or salt may range from about 0.001 to about 10%, preferably between about 0.8 and about 2.5%, optimally between about 1 and 1.5% by weight.

The second class of keratolytic agent is the $C_2$–$C_{25}$ α-hydroxy alkanoic acids. Illustrative of this group of materials are glycolic, lactic, α-hydroxyoctanoic acids and salts thereof. The salts may be selected from alkalimetal, ammonium and $C_1$–$C_{20}$ alkyl or alkanolammonium counterions. Levels of α-hydroxyalkanoic acids may range from about 0.001 to about 10%, preferably between about 0.2 and 1%, optimally between about 0.4 and 0.5% by weight.

Compositions of the present invention may either be aqueous or anhydrous. Preferably the compositions are aqueous, especially water and oil emulsions of the W/O or O/W variety. Water when present will be in amounts which may range from about 5 to about 90%, preferably from about 35 to about 65%, optimally between about 40 and 50% by weight.

Besides water, relatively volatile solvents may also be incorporated within compositions of the present invention. Most preferred are monohydric $C_1$–$C_3$ alkanols. These include ethyl alcohol, methyl alcohol and isopropyl alcohol. The amount of monohydric alkanol may range from about 5 to about 50%, preferably from about 15 to about 40%, optimally between about 25 to about 35% by weight.

Emollient materials in the form of silicone oils and synthetic esters may be incorporated into compositions of the present invention. Amounts of the emollients may range anywhere from about 0.1 to about 30%, preferably between about 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as emollient materials include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl branched or straight chain esters of fatty acids having 9 to 22 carbon atoms. Examples thereof include isononyl isonanonoate, oleyl myristate, oleyl stearate, and oleyl oleate.

(2) Ether-esters such as fatty acid esters of ethoxylated fatty alcohols such as:

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate, arachnidyl behenate, arachdyl erucite and arachdyl candelirate (5) Sterols esters, of which cholesterol fatty acid esters are examples thereof.

(6) Ethoxylated esters of branched or straight chain fatty acids such as $C_{12-20}$ Acid PEG-8 ester.

(7) Glycosidic ethers of straight or branched chain fatty acids, such as cetearyl glycoside, arachctyl glycoside and erucyl glycoside.

The most preferred esters are octyldodecyl neopentanoate (available as Elefac I-205®) and isononyl isononanoate (Available as Solacos 99® and Dermol 99®.

Fatty acids having from 10 to 30 carbon atoms may also be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Collectively the water, solvents, silicones, esters, fatty acids, humectants and/or thickeners are viewed as cosmetically acceptable carriers for the compositions of the invention. Total amount of carrier will range from about 1 to 99.9%, preferably from about 80 to 99% by weight.

Cosmetic compositions of the present invention may be in any form. These forms may include lotions, creams, roll-on formulations, mousses, aerosol sprays and pad-applied formulations.

Surfactants may also be present in cosmetic compositions of the present invention. Total concentration of the surfactant will range from about 0.1 to about 40%, preferably from about 1 to about 20%, optimally from about 1 to about 5% by weight of the total composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from about 2 to about 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, $C_8$–$C_{20}$ alkyl ether phosphates and combinations thereof.

Sunscreen actives may also be included in compositions of the present invention. Particularly preferred are such materials as ethylhexyl p-methoxycinnamate, available as Parsol MCX, and benzophenone-3, also known as Oxybenzone. Inorganic sunscreen actives may be employed such as microfine titanium dioxide, polyethylene and various other polymers. Amounts of the sunscreen agents will generally range from about 0.1 to about 30%, preferably from about 2 to about 20%, optimally from about 4 to about 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be present in the cosmetic compositions. Among them may be the water-insoluble vitamins such as Vitamin A Palmitate, Vitamin E Acetate and DL-panthenol.

Another adjunct ingredient can be that of an enzyme. Particularly preferred is superoxide dismutase, commercially available as Biocell SOD from the Brooks Company, USA.

Natural vegetable materials from renewable resources are often desirable in cosmetic compositions. For instance, cosmetic compositions of the present invention may include β-glucan derived from oats, commercially available under the trademark Microat SF from Nurture Inc., Missoula, Mont.

Colorants, fragrances, opacifiers and abrasives may also be included in compositions of the present invention. Each of these substances may range from about 0.05 to about 5%, preferably between 0.1 and 3% by weight.

The following Examples will more fully illustrate the embodiments of this invention. All parts, percentages and proportions referred to herein and in the appended claims are by weight unless otherwise indicated.

EXAMPLE 1

A typically formulated whitening cream gel according to the present invention is described below:

| Ingredient | % w/w |
|---|---|
| Deionized water | 56.8 |
| Disodium EDTA | 0.100 |
| Methylparaben | 0.200 |
| Xanthan gum | 0.3 |
| Butylene glycol | 0.750 |
| Seppigel(R) 305 | 1.5 |
| Caprylic/capric/linoleic triglycerides | 0.5 |
| Ticapryl citrate | 0.5 |
| Eumulgin B-2(R) | 0.5 |
| Xalifin 15(R) | 1.75 |
| Montanov 68(R) | 2.000 |
| Cetyl ricinoleate | 0.350 |
| C10–18 triglyceride | 1.85 |
| Propylparaben | 0.100 |
| Squalene | 1.000 |
| Diisopropyl dilinoleate | 0.500 |
| Vitamin E acetate | 0.15 |
| Fomblin HC 25(R) | 0.500 |
| Dow Corning 200 (100 CST) | 3.15 |
| Dow Corning 1402 | 1.000 |
| Dow Corning 344 | 6.5 |
| Phenoxyethanol | 0.400 |
| Deionized water | 6.000 |
| Placenta extract | 3.000 |
| Sodium hyaluronate | 2.100 |
| Fruit Ext. blend | 5.000 |
| Sodium Salicylate | 0.05 |
| Triethanolamine | 1.75 |

EXAMPLE 2

Another typically formulated whitening cream gel according to the present invention is described below:

| Ingredient | % w/w |
|---|---|
| Deionized water | 58.8 |
| Disodium EDTA | 0.100 |
| Methylparaben | 0.200 |
| Xanthan gum | 0.3 |
| Butylene glycol | 0.750 |
| Seppigel(R) 305 | 1.5 |
| Caprylic/capric/linoleic triglycerides | 0.5 |
| Ticapryl citrate | 0.5 |
| Eumulgin B-2(R) | 0.5 |
| Xalifin 15(R) | 1.65 |
| Montanov 68(R) | 2.000 |
| Cetyl ricinoleate | 0.350 |
| C10–18 triglyceride | 1.85 |
| Propylparaben | 0.100 |
| Squalene | 1.000 |
| Diisopropyl dilinoleate | 0.500 |
| Vitamin E acetate | 0.15 |
| Fomblin HC 25(R) | 0.500 |
| Dow Corning 200 (100 CST) | 3.15 |
| Dow Corning 1402 | 1.000 |
| Dow Corning 344 | 6.5 |
| Phenoxyethanol | 0.400 |
| Deionized water | 6.000 |
| Placenta extract | 3.000 |
| Sodium hyaluronate | 2.100 |
| Fruit Ext. blend | 5.000 |
| Sodium Salicylate | 0.05 |
| Triethanolamine | 1.75 |
| Uvinul MS-40 | 0.10 |
| Citric acid, anhydrous | 0.08 |
| Sodium citrate (dihydrate) | 0.12 |
| Fragrance | 0.1 |

EXAMPLE 3

A typically formulated sunscreen lotion according to the present invention is described below:

| Ingredient | % w/w |
|---|---|
| Deionized water | 56.8 |
| Disodium EDTA | 0.100 |
| Methylparaben | 0.200 |
| Octyl methoxycinnamate | 5.0 |
| Oxybenzone | 3.0 |
| Xanthan gum | 0.3 |
| Butylene glycol | 0.4 |
| Seppigel(R) 305 | 1.000 |
| Caprylic/capric/linoleic triglycerides | 0.5 |
| Ticaprylyl citrate | 0.5 |
| Eumulgin B-2(R) | 0.500 |
| Xalifin 15(R) | 1.65 |
| Montanov 68(R) | 2.000 |
| Cetyl ricinoleate | 0.350 |
| C10–18 triglyceride | 1.85 |
| Propylparaben | 0.100 |
| Squalene | 1.000 |
| Diisopropyl dilinoleate | 0.500 |
| Vitamin E acetate | 0.15 |
| Fomblin HC 25(R) | 0.500 |
| Dow Corning 344 | 6.000 |
| Phenoxyethanol | 0.400 |
| Deionized Water | 6.000 |
| Placenta extract | 3.000 |
| Sodium hyaluronate | 2.100 |
| Fruit Ext. blend B-2367 | 2.0 |

-continued

| Ingredient | % w/w |
|---|---|
| Sodium Salicylate | 0.05 |
| Triethanolamine | 1.75 |

EXAMPLE 4

Two samples of the composition were prepared as described in Example 1 having either 1.5% Montanov 68 or 2.0% Montanov 68 the samples were stored at 25° C., 37° C., 43° C., 50° C. and under alternating temperatures (40° C. to 43° C). A Brookfield Viscosity, Spindle #3 (rpm at 25° C.) was used to measure viscosities.

It was observed that after only 1 week at 50° C. the sample containing 1.5% Montanov 68 phase separated. The sample containing 20% Montanov 68 remained stable for at least 4 weeks.

EXAMPLE 5

To demonstrate the criticality of the three components of the emulsifying system in the required ratios the following samples are prepared and tested for stability as described in Example 4 above.

| | % w/w | | | |
|---|---|---|---|---|
| Ingredient | Sample 1 | Sample 2 | Sample 3 | Sample 4 |
| Deionized water | 65.1 | 65.1 | 65.1 | 65.1 |
| Disodium EDTA | 0.1 | 0.1 | 0.1 | 0.1 |
| Methylparaben | 0.2 | 0.2 | 0.2 | 0.2 |
| Xanthan gum | 0.3 | 0.3 | 0.3 | 0.3 |
| Butylene glycol | 0.75 | 0.75 | 0.75 | 0.75 |
| Seppigel(R) | 1.0 | 1.0 | 1.0 | 1.0 |
| Propylene glycol dicaprulate/dicaprate | 0.5 | 0.5 | 0.5 | 0.5 |
| Ticapryl citrate | 0.5 | 0.5 | 0.5 | 0.5 |
| Eumulgin B-2 | 0.5 | 0.5 | — | 0.5 |
| Xalifin 15(R) | 1.65 | 1.65 | 1.65 | — |
| Montanov 68(R) | 2.0 | — | 2.0 | 2.0 |
| Cetyl ricinoleate | 0.350 | 0.350 | 0.350 | 0.350 |
| Nesato(R) | 1.85 | 1.85 | 1.85 | 1.85 |
| Propylparaben | 0.100 | 0.100 | 0.100 | 0.100 |
| Squalene | 1.000 | 1.000 | 1.000 | 1.000 |
| Schercemoldid(R) | 0.500 | 0.500 | 0.500 | 0.500 |
| Vitamin E acetate | 0.15 | 0.15 | 0.15 | 0.15 |
| Fomblin HC 25(R) | 0.500 | 0.500 | 0.500 | 0.500 |
| Dow Corning 200 D(100 CST) | 3.15 | 3.15 | 3.15 | 0.15 |
| Dow Corning 1401 | 1.0 | 1.0 | 1.0 | 1.0 |
| Dow Corning 344 | 6.5 | 6.5 | 6.5 | 6.5 |
| Phenoxyethanol | 0.4 | 0.4 | 0.4 | 0.4 |
| Placental extract | 3.0 | 3.0 | 3.0 | 3.0 |
| Actiglide J (Special) | 2.1 | 2.1 | 2.1 | 2.1 |
| Fruit ext. blend | 5.0 | 5.0 | 5.0 | 5.0 |
| Sodium salicylate | 0.05 | 0.05 | 0.05 | 0.05 |
| Fragrance | 0.06 | 0.06 | 0.06 | 0.06 |
| Octyl methoxycinnamate | 5.0 | 5.0 | 5.0 | 5.0 |
| Oxbenzone | 3.0 | 3.0 | 3.0 | 3.0 |
| Triethanolamine 99% | 1.75 | 1.75 | 1.75 | 1.75 |

Stabilities of the four samples were assessed both visually and instrumentally the results are shown in the table below:

| T | Sample 1 | | | | Sample 2 | | | | Sample 3 | | | | Sample 4 | | | |
|---|---|---|---|---|---|---|---|---|---|---|---|---|---|---|---|---|
| | 1w | 2w | 3w | 4w | 1w | 2w | 3w | 4w | 1w | 2w | 3w | 4w | 1w | 2w | 3w | 4w |
| RT | A | A | A | A | U | U | U | U | A | A | A | A | A | A | A | A |
| 4° | A | A | A | A | U | U | U | U | A | A | A | A | A | A | A | A |
| 37° | A | A | A | A | U | U | U | U | A | A | A | U | A | A | A | U |
| 43° | A | A | A | A | U | U | U | U | U | U | U | U | U | U | U | U |
| 50° | A | A | A | A | U | U | U | U | U | U | U | U | U | U | U | U |
| ALT | A | A | A | A | U | U | U | U | U | U | U | U | U | U | U | U |

In the table "U" denotes an unacceptable product having a grainy structure, separation and/or low viscosity recovery.

"A" in the table denotes a homogenous structure without phase separation.

In summary only Sample 1 containing all three components of the claimed emulsifying system provided a consusmer acceptable product under both normal and extreme storage conditions.

In contrast, Samples 2, 3 and 4 containing only two of the three emulsifying components provided either unacceptable products or products which became unstable in storage.

What is claimed:

1. A cosmetic composition comprising:

a) from 0.05 to 3 wt. % of a thickening polymer selected from the group consisting of sclerotium gum, xanthan gum and mixtures thereof;

b) an emulsifying system comprising:

i) from about 1.5 to about 8% by weight of a polyethylene glycol ether of cetearyl alcohol having a formula $$R(OCH_2)_nOH$$

wherein n is 10–30, ii) from about 0.1 to about 5% by weight of a $C_{12}$ to $C_{20}$ fatty acid polyethylene glycol ester having from 5 to 10 EOs, and iii) from about 0.15 to about 4.5% by weight of a mixture of a cetearyl alcohol and a cetearyl glycoside in a weight ratio of 65–90 to 35–10; and c) from 1 to 99.9% of a cosmetically acceptable carrier.

2. A cosmetic composition according to claim 1, wherein the ratio of (i) to (ii) to (iii) is from about 2:6:5 to about 3:7:6.

3. A composition according to claim 1, wherein the final composition has a pH range of less than about 8.

4. A composition according to claim 1, wherein the fatty acid polyethylene glycol ester is a $C_{12-20}$ acid PEG-8 ester.

5. A composition according to claim 1, further comprising from about 0.001 to about 1% by weight of water insoluble vitamins.

6. A composition according to claim 5, wherein the vitamins are selected from the group consisting of vitamin E acetate, vitamin A palmitate and vitamin E linoleate.

* * * * *